United States Patent [19]

Kretschmer et al.

[11] Patent Number: 4,945,916
[45] Date of Patent: Aug. 7, 1990

[54] OPTICAL DEVICE FOR THE SIMULTANEOUS DETECTION OF HEART AND RESPIRATORY MOVEMENTS

[75] Inventors: Sylvain Kretschmer, Paris; Jean-Paul Do-Huu, Ivry; Francois Micheron, Gif Sur Yvette, all of France

[73] Assignee: Thomson CSF, Paris, France

[21] Appl. No.: 112,672

[22] Filed: Oct. 14, 1987

[30] Foreign Application Priority Data

Oct. 14, 1986 [FR] France ................. 86 14260

[51] Int. Cl.⁵ ......................................... A61B 5/0205
[52] U.S. Cl. ..................... 128/671; 128/714; 128/721; 128/774; 128/782
[58] Field of Search ............... 128/653, 665, 666, 670, 128/671, 687, 689, 690, 714, 721, 774, 782; 356/447

[56] References Cited

U.S. PATENT DOCUMENTS

| | | | |
|---|---|---|---|
| 3,517,999 | 6/1970 | Weaver | 128/721 |
| 4,664,129 | 5/1987 | Helzel et al. | 128/721 |
| 4,694,837 | 9/1987 | Blakeley et al. | 128/671 |
| 4,803,992 | 2/1989 | Lemelson | 128/666 |

FOREIGN PATENT DOCUMENTS

| | | | |
|---|---|---|---|
| 1570640 | 6/1969 | France | 128/721 |
| 1219047 | 3/1986 | U.S.S.R. | 128/690 |

OTHER PUBLICATIONS

Willis, "Respiration Transducer", IBM Technical Disclosure Bulletin, vol. 6, No. 6, Nov. 1963, p. 13.

Primary Examiner—Ruth S. Smith
Attorney, Agent, or Firm—Oblon, Spivak, McClelland, Maier & Neustadt

[57] ABSTRACT

The device comprises a sensor with a mirror coupled to a diaphragm used to shift the mirror according to the patient's heart and thorax movements. A light generator illuminates the mirror. An electro-optical detector converts the intensity of the light rays reflected by the mirror into an electrical signal and a processing circuit generates output signals indicative of heart and respiratory movements.

10 Claims, 5 Drawing Sheets

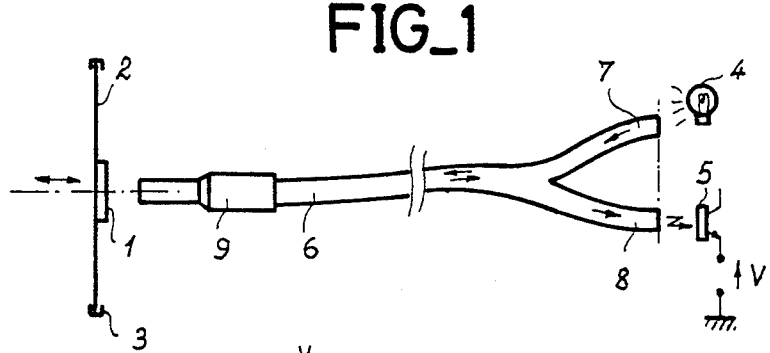
FIG_1
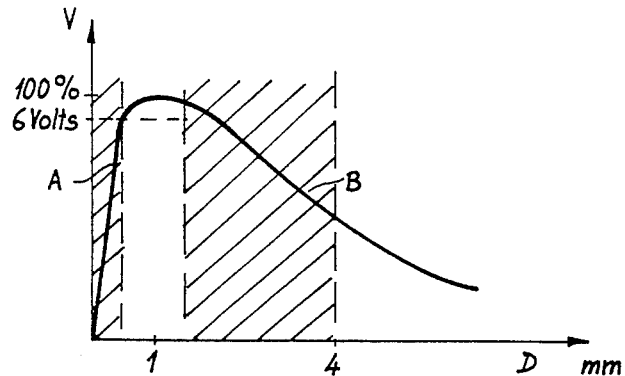
FIG_2
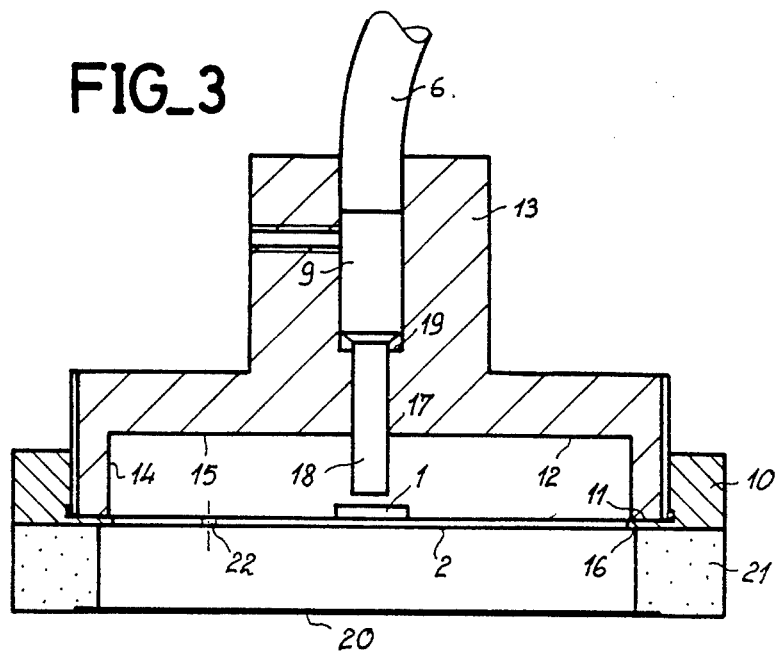
FIG_3

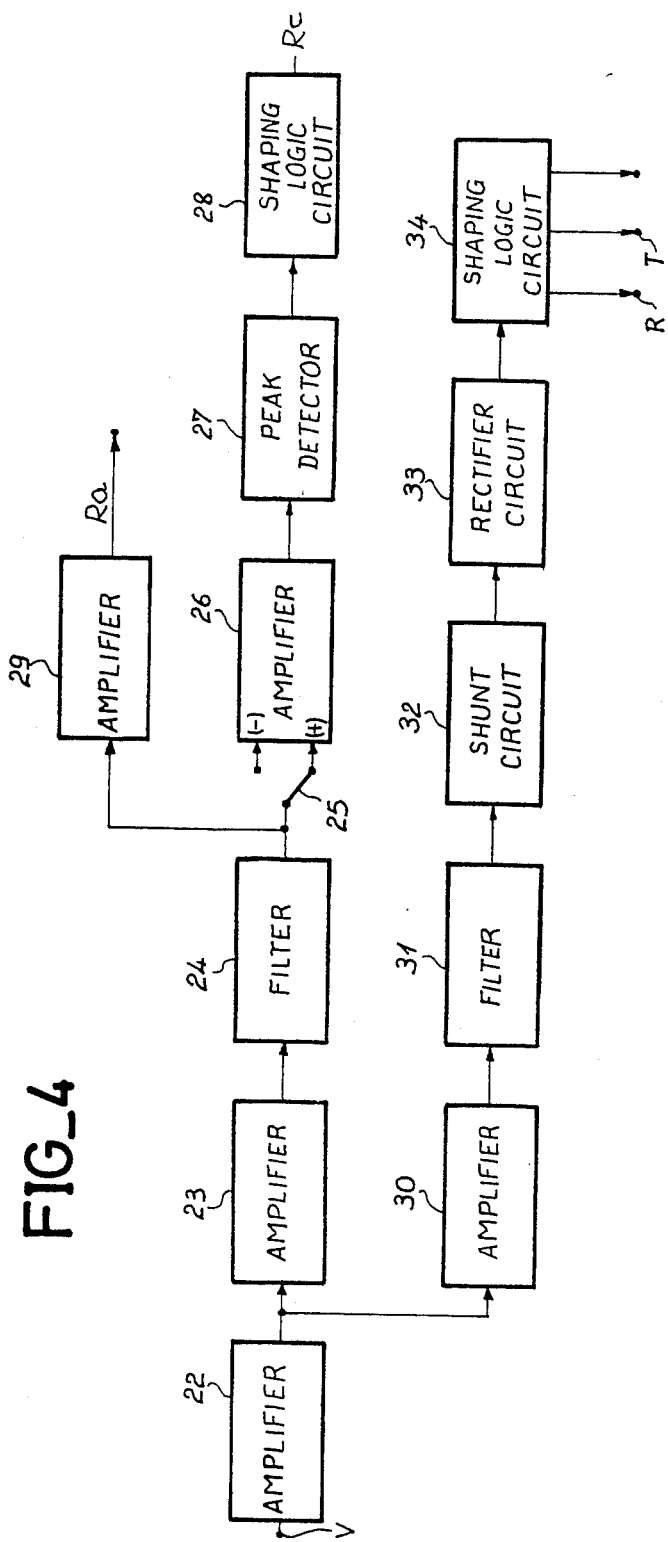
FIG_4

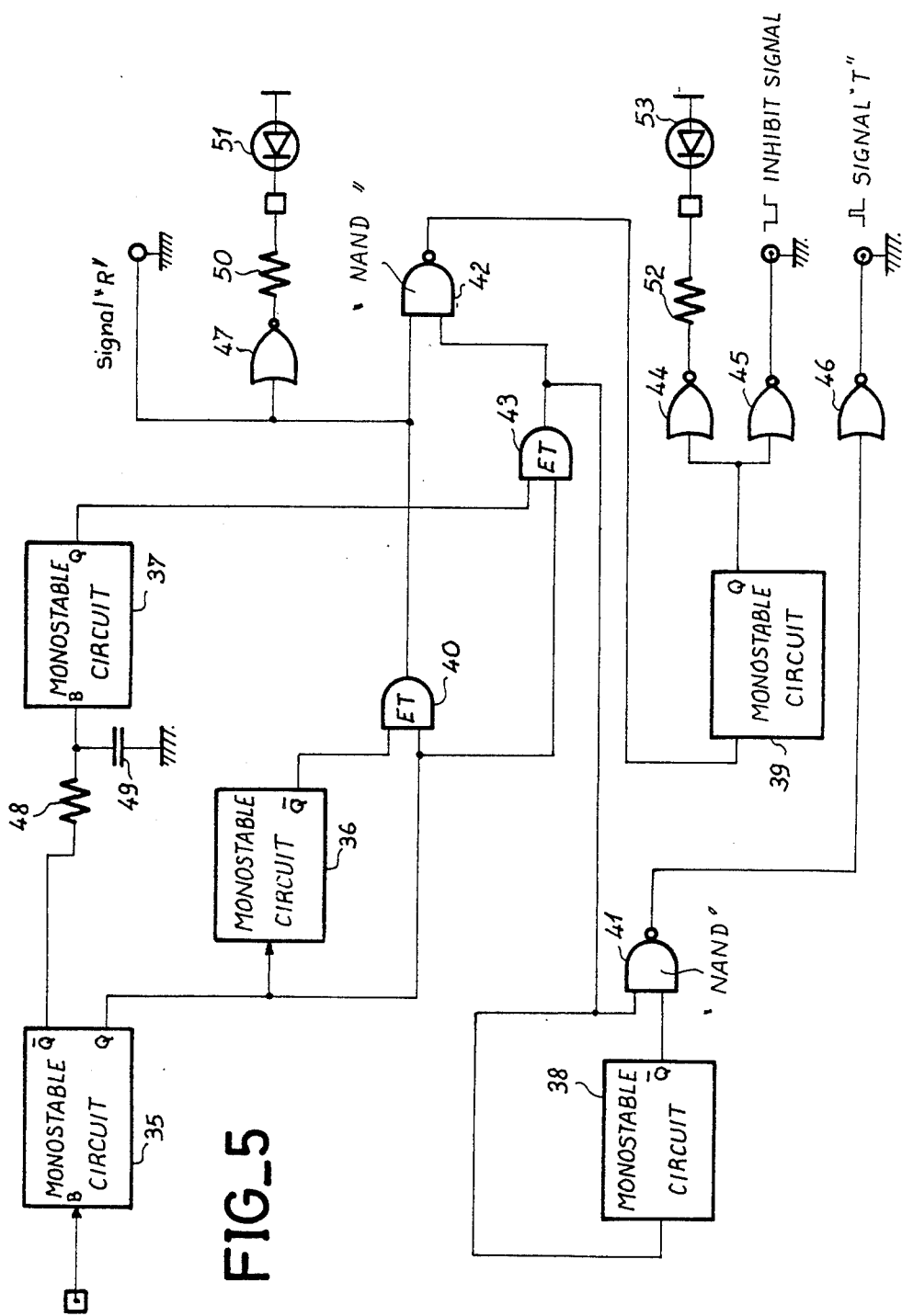
FIG_5

FIG_6
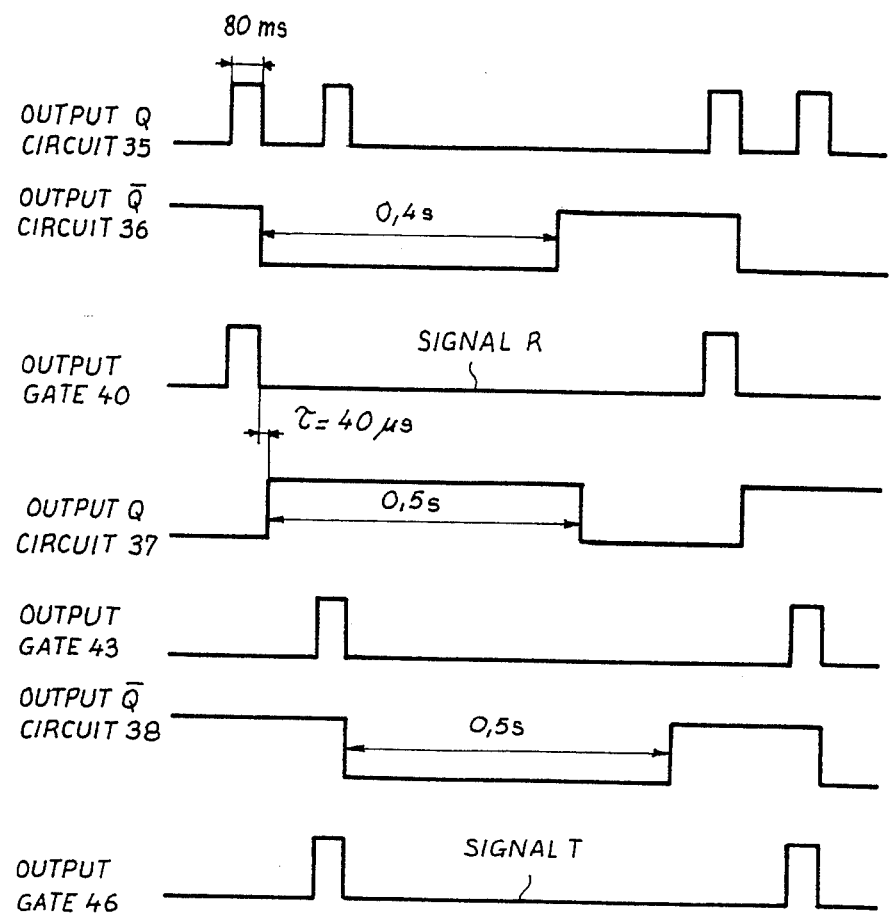

FIG_7
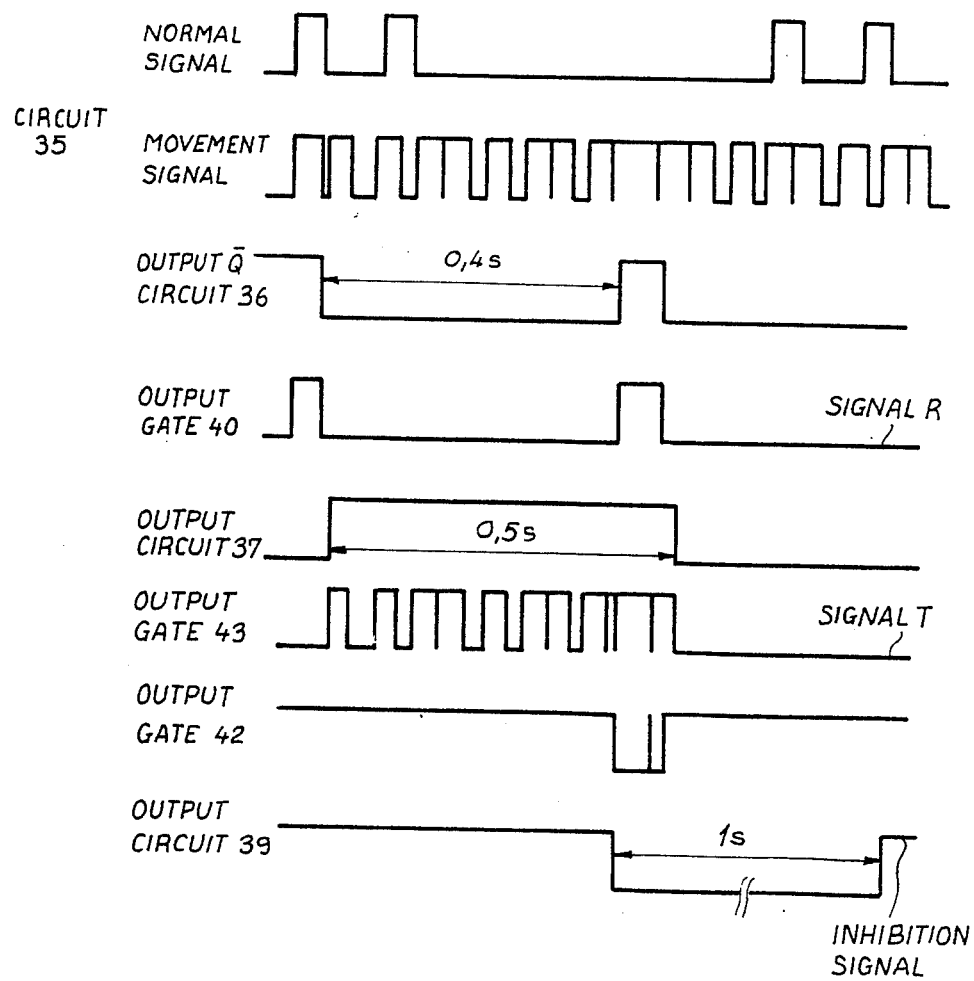

OPTICAL DEVICE FOR THE SIMULTANEOUS DETECTION OF HEART AND RESPIRATORY MOVEMENTS

BACKGROUND OF THE INVENTION

1. Field of the Invention

The present invention pertains to an optical device for the simultaneous detection of cardiac and respiratory movements and to the use of the device for synchronizing nuclear magnetic resonance imaging instruments, more commonly known as MRI instruments.

2. Description of the Prior Art

In prior art methods, the quality of the images given by these devices is improved by synchronizing them with the heart and respiratory rhythms of the patients examined, by means of signals from electrocardiographs.

However, the electrodes and metallic connecting cables used to convey the synchronizing signals deform the field lines of the powerful magnetic and electrical fields radiated, and the quality of the images obtained is affected. This results in a major disadvantage for physicians who risk making false diagnoses.

In an alternative embodiment of the method described above, the synchronization is done with signals from acoustic and pneumatic stethoscopes. These stethoscopes have the advantage, when compared with electrocardiographs, of not interfering with the magnetic and electromagnetic fields. But they remain sensitive to ambient acoustic noise, and the propagation time of the pressure wave in the connecting tubes which link them to the MRI instruments results in a phase shift, incompatible with its function and difficult to compensate for, between the synchronizing signals and the corresponding cardiac and respiratory activities.

3. Summary of the Invention

An object of the invention is to remove the above disadvantages.

To this end, an object of the invention is an optical device for the simultaneous detection of heart and respiratory movements, a device comprising a sensor with a movable mirror coupled to means used to shift the mirror by the patient's heart and thorax movements, a light generator to illuminate the mirror and electro-optical means to convert the intensity of the light beams reflected by the mirror into an electrical signal.

BRIEF DESCRIPTION OF THE DRAWINGS

Other features and advantages of the invention will appear from the following description, made with reference to the appended drawings, of which:

FIG. 1 shows the principle of the embodiment of the device according to the invention;

FIG. 2 is a graph showing the functioning of the device of FIG. 1;

FIG. 3 is a complete embodiment of the sensor;

FIG. 4 is an embodiment of electronic processing means;

FIG. 5 is an embodiment of a synchronization signal shaping logic circuit;

FIGS. 6 and 7 are timing diagrams to illustrate the functioning of the logic circuit shown in FIG. 5.

DETAILED DESCRIPTION OF THE INVENTION

The device according to the invention, shown in a simplified form in the schematic diagram of FIG. 1, is used to pick up cardiac noises as an acoustic stethoscope would do in stethoscopic phonocardiography with, however, the advantage of eliminating the propagation delays inherent in sound waves which are propagated in the connecting tube of these stethoscopes.

According to the embodiment shown, the sensor of the device according to the invention consists of a mirror 1 bonded to a diaphragm 2 which is kept stretched by its edges on a frame 3. The mirror 1 is illuminated by a light generator 4, which may comprise a laser diode or any equivalent device. The light, reflected by the mirror, is sent back towards an electro-optical detector 5 which may comprise a phototransistor or any equivalent device. The light is carried in both directions of propagation by a Y-shaped light guide 6, interposed between the mirror 1, on the one hand, and the light generator 4 and the electro-optical detector 5, on the other. To do this propagation, the light guide 6 is made up of two distinct bundles of optic fibers 7 and 8, joined to each other by a sheath 9 at one of their ends facing the mirror 1. The other ends of the bundles 7 and 8 are separated from each other so that the light given by the generator 4 can be introduced into one of the bundles (the bundle 7 for example) and so that the said light can be detected at the end of the other bundle (the bundle 8 for example) by the electro-optical detector 5. For example, without limiting the scope of the invention, the light guide 6 may comprise an optic fiber probe of the type marketed under the reference BFS-CGP2 by the French company FORT.

The light reflected by the mirror 1, which reaches the end of the bundle 8, causes a voltage V to appear at the output of the electro-optical detector 5. The amplitude of the voltage V is modulated in accordance with the movement D of the mirror 1 along the longitudinal direction of the light guide 6. A curve representing the changes in the voltage V according to the movement D is shown in FIG. 2. This curve has two approximately linear zones A and B which exhibit two different levels of sensitivity.

In the zone A, the voltage V changes between a value of zero and a value of about 6 volts close to its maximum value for movements D ranging from 0 to 0.5 mm., and its sensitivity is about 12 volts per millimeter. By contrast, in the zone B, the voltage changes in the opposite direction, from a value of 6 volts, close to the maximum value, to an attenuated value of about half, for movements ranging from 1 to 4 mm., and the sensitivity is about 1 volt per millimeter. These results show that the device of the invention can be advantageously used to detect respiratory movements in human beings because the movements of the mirror 1, which characterize the zone B, have amplitudes which are quite comparable to those that might be expected of a respiratory movement when placing the diaphragm 2 directly upon the chest of a patient. However, it also appears that the sensitivity of this zone is too low to reveal the cardiac pulsations which cause movements of only a few hundredths of a millimeter at the surface of the thorax. Thus, the zone B can be used to obtain a useful signal of only a few tens of millivolts, and it would be very difficult to separate this signal from the ambient electronic noise.

By contrast, the zone A offers this possibility since the sensitivity in this zone is sufficient to extract a useful signal which is greater than the inherent noise of the electronic circuits. However, the very small dynamic range (smaller than 0.5 mm.) of the movements of the mirror prevents the diaphragm 2 from being placed in direct contact with the patient's chest. This difficulty is surmounted in the invention by placing an intermediate ring between the diaphragm 2 and the patient's chest. An example of a sensor made according to this principle is shown in FIG. 3. In FIG. 3, elements similar to those of FIG. 1 are given the same references. In this example, the diaphragm 2 is fixed by a threaded ring 10 to the outer edge 11 of a cylindrical cavity 12, made in the body of a supporting part 13. The cavity 12 is bounded by a cylindrical wall 14 and two parallel plane surfaces perpendicular to the axis of revolution of the cavity. A plane surface is formed by the bottom 15 of the cavity, and the second plane surface is formed by the diaphragm 2 which is supported on the outer edge 11 by a shoulder 16 of the ring 10.

The bottom 15 is pierced in its center and in the direction perpendicular to its plane with a hole 17 in which the end 18 of the light guide 6 is engaged. The hole 17 also has a shoulder 19 on which an end of the sleeve 9 is supported. The end 18 of the light guide 6 ends in the interior of the cavity 12. The diaphragm 2 is positioned on the edges of the cavity so that the mirror 1 which it supports directly faces the end 18 of the light guide. To enable the detection of cardiac movements without the movements being disturbed by the respiratory movement, a second diaphragm 20 is coupled to the first diaphragm 2 by a supporting frame or a flexible ring 21 fixed so that it is supported by the ring 10. Furthermore, a small hole 22 is drilled in the diaphragm 2 to balance the air pressure on either side of the diaphragm 2 and give the unit the behaviour of a high-pass acoustic filter in order to eliminate frequencies below those of the respiration caused, for example, by temperature variations.

During use, the diaphragm 20 is kept in contact with the skin by a strap (not shown) which is tightened lightly around the thorax and takes support from the body of the supporting part 13. This enables the cardiac sound wave to reach the diaphragm 2 through the diaphragm 20, and enables the respiratory movement to exert pressure through the strap crushing the flexible ring 21 on the chest in varying degrees. These movements are transmitted to the mirror 1 by the volume of air imprisoned between the two diaphragms 20 and 2. Naturally, for the MRI application envisaged, the entire sensor just described should be made with non-magnetic materials and, for this, plastic materials could be used, for example the material known by the brand name DELRIN manufactured by E. I. DUPONT DE NEMOURS & CO.

An embodiment of the electronic processing means enabling the device of the invention to be used to synchronize nuclear magnetic resonance imaging instruments is described below with reference to FIG. 4. These means comprise a first channel, consisting of elements 23 to 29, designed to extract the signals that are representative of the respiratory rhythm, and a second channel, consisting of the elements 30 to 34, designed to extract the signals representative of the cardiac rhythm, from the V-shaped signal given by the photoelectric sensor 5 of FIG. 1 and amplified by an amplifier 22, common to both channels.

The first channel comprises an adjustable-gain amplifier 23, a low-pass filter 24, a pole-changing switch comprising a switch 25 and a differential amplifier 26, a peak detector 27, a shaping logic circuit 28 and an amplifier 29.

The amplifier 23 is coupled to the output of the amplifier 22 and is used to adapt the first processing channel to the sensitivity of the sensor described above. The low-pass filter 24 has a cut-off frequency of 4 hertz and is used to attenuate cardiac noises so as to give preference to the signal from the thorax due to respiration, the frequency of the signal being about 0.2 hertz. The low-pass filter receives the signals given by the amplifier 23 and transmits them filtered at the inverter input marked "−" or non-inverter, input, marked "+" of the amplifier 26 through the switch 25. By activating the switch 25 at the inputs marked "−" or "+" of the amplifer 26, the synchronization point can be chosen at either the breathing-in or the breathing-out stage of the respiratory movement. The output of the amplifier 26 is coupled to the input of the peak detector 27 so as to obtain, with precision and in a reproducible way, the instant marking the start of a breathing-in stage or a breathing-out stage of the respiratory cycle, $R_c$, by corresponding pulses which are, if necessary, shaped by the shaping logic circuit 28. Finally, an impedance amplifier-adaptor 29 is also coupled to the output of the filter 24 so as to restore the analog signal $R_a$ corresponding to the respiratory cycle.

The second channel, consisting of the elements 30 to 34, comprises the following elements, serially connected in the order given: a gain-adjusting amplifier 30, a pass-band filter 31 with cut-off frequencies of 0.5 and 200 hertz for example, a second-order analog shunt circuit 32, a rectifier circuit 33 and a shaping logic circuit 34. As with the first channel, the amplifier 30 is coupled to the output of the amplifier 22 and has an adjustable gain to adapt the processing line of the second channel to sensitivity level of sensor used. The pass-band filter 31 eliminates the low-frequency respiratory signal, the high-frequency unwanted signals and the ambient noises above 200 hertz from the signal given by amplifier 30, letting through the useful signal representing the cardiac rhythm with a frequency range within the useful band and not exceeding 200 hertz. The analog shunt circuit 32 receives cardiac pulses filtered by the filter 31 to give the two pulses corresponding to the noises B1 and B2 signifying the waves R and T, defined in electrocardiography as being the waves marking the end of the diastole and the systole respectively. After rectification by the rectifier 33, the shaping logic circuit 34 eliminates the parasite pulses and selects signals, corresponding respectively to the waves R and T, Another logic device located inside the shaping logic circuit 34 is used to generate the inhibit signal.

An embodiment of the shaping logic circuit 34 and its operation are described below with reference to the FIGS. 5, 6 and 7.

The shaping logic circuit 34 shown in FIG. 5 comprises a set of monostable circuits 35 to 39 coupled to a set of logic gates 40 to 47. A direct output marked Q of the monostable circuit 35 is directly connected to the input of the monostable circuit 36 and to a first input of the gate 40 formed by an AND gate with two inputs, the second input of which is connected to the additional output marked $\overline{Q}$ of the monostable circuit 36. The input of the monostable circuit 37 is connected to the additional output marked $\overline{Q}$ of the monostable circuit 35 through a delay line comprising a resistor 48 and a capacitor 49. The gates 41 and 42 are NAND gates with two inputs. The gate 43 is an AND gate. It has two inputs which are respectively connected to an output marked Q of the monostable circuit 37 and the output marked Q of the monostable circuit 35. The AND gate 40 prepares the signal R and applies this signal to a first input of the NAND gate 42 and to a display device comprising the gate 47, a resistor 50 and a light-emitting diode 51 which are series-mounted. The second input of the NAND gate 42 is connected to the output of the AND gate 43, to an input of the monostable circuit 48 and a first input of the NAND gate with two inputs 41. The additional output, marked $\overline{Q}$, of the monstable circuit 38 is connected to a second input of the NAND gate 41, the output of which gives the signal T through the inverter gate 46. The monostable circuit 39 is triggered at its input by the signal given by the output of the NAND gate 42, and its output marked Q gives the inhibition signal firstly to a display device formed by the gate 44, a resistor 52 and a light-emitting diode, all series-mounted, and secondly to the input of the gate 45. The monostable circuits have time lags of 80 ms, 0.4 s, 0.5 s, 0.46 s and 1 s respectively. The delay line formed by the resistor 48 and the capacitor 49 has the structure of a first-order low-pass filter and has a time constant of 40 microseconds. The timing diagrams, which represent the preparation of the R and T signals on the one hand, and of the inhibition signal on the other, are shown in the FIGS. 6 and 7 respectively. In these figures, and especially in FIG. 7, it can be seen that the output of the circuit 35 has a signal comprising the pulses R and T of the cardiac rhythm, possibly with a few unwanted pulses reflecting a movement by the patient. The circuit 36, associated with the gate 40, is used to extract only the pulse R. The circuits 37 and 38, associated with the gate 43, is used to extract the pulse T.

The inhibition signal is formed by the gate 42 and the circuit 39. The formation of that signal uses the fact that, if the patient moves, the shunt signal given by the differentiating circuit 32 takes the shape of a pulse train with the pulses R and T present simultaneously. The gate 42 then sets off an inhibition signal, the duration of which is fixed at one second by the circuit 39.

What is claimed is:

1. An optical device for the simultaneous detection of heart and respiratory movements, comprising a sensor comprising a movable mirror coupled to means used to move the mirror according to heart and respiratory movements, a light generator coupled to light guide means, to illuminate the mirror, and electro-optical means also coupled to the light guide means, to convert intensity of a light beam reflected by the mirror into an electrical signal, and processing means for receiving the electrical signal and converting this signal into output signals respectively indicative of heart and respiratory movements.

2. A device according to claim 1, wherein the means used to move the mirror comprise a first diaphragm supporting the mirror and a supporting frame in which a cavity is formed; the first diaphragm being fixed to the supporting frame and closing the cavity.

3. A device according to claim 2, comprising a second diaphragm fixed to the supporting frame and parallel to the first diaphragm so defining a space between said first and second diaphragms.

4. Device according to the claim 1 wherein the supporting frame is made of a pliant material.

5. Device according to the claim 4 wherein the first diaphragm blocks the cavity and is drilled with a hole so that the space between the two diaphragms can communicate with the cavity and so as to establish a high-pass acoustic filter with the cavity and the second diaphragm.

6. A device according to claim 5, wherein said light guide means is an optic fiber having a Y-shaped first end forming two first end faces respectively coupled to the light generator and to the electro-optical converting means, and having a second end engaged in the supporting frame with an end face in front of the mirror.

7. A device according to claim 1, wherein the processing means comprise a first channel comprising the following elements series-connected in the order given: an amplifier with gain adjustment according to sensitivity of the sensor, a low pass filter for attenuating, in said electrical signal, signals generated by heart movements, and thus selecting signals generated by respiratory movements, a pole-changing switch to choose the synchronizing instant at breathing-in or breathing-out stages, a peak voltage detector and a shaping circuit for delivering an output signal indicative of a precise and reproducible instant in respiratory cycles.

8. A device according to claim 7, wherein said first channel further comprises a second amplifier coupled to the output of said low pass filter for delivering an output analog signal indicative of the respiratory rhythm.

9. A device according to claim 7, wherein the processing means comprise a second channel comprising the following elements series-connected in the order given: a gain-adjusting amplifier, a pass band filter for eliminating, in said electrical signal, signals generated by respiratory movements and unwanted signals and/or ambient noises above the highest heartbeat frequencies, a second order analog shunt circuit, a rectifier circuit and a shaping logic circuit for delivering two output pulse signals indicative of electrocardiography R and T waves.

10. A device according to claim 9, wherein the shaping logic circuit has a further output for delivering an inhibiting signal when detected movements have amplitudes which are not indicative of heart or respiratory movements.

* * * * *